(12) United States Patent
Shekhawat et al.

(10) Patent No.: US 11,975,303 B2
(45) Date of Patent: May 7, 2024

(54) ELECTROMAGNETIC FIELD-ASSISTED METHOD FOR CHEMICAL CONVERSION

(71) Applicant: United States Department of Energy, Washington, DC (US)

(72) Inventors: Dushyant Shekhawat, Morgantown, WV (US); David A Berry, Morgantown, WV (US); Mark W Smith, Morgantown, WV (US); Christina Wildfire, Morgantown, WV (US); Victor Abdelsayed, Morgantown, WV (US)

(73) Assignee: United States Department of Energy, Washington, DC (US)

( * ) Notice: Subject to any disclaimer, the term of this patent is extended or adjusted under 35 U.S.C. 154(b) by 766 days.

(21) Appl. No.: 16/355,122

(22) Filed: Mar. 15, 2019

(65) Prior Publication Data

US 2019/0282992 A1    Sep. 19, 2019

Related U.S. Application Data

(60) Provisional application No. 62/643,285, filed on Mar. 15, 2018.

(51) Int. Cl.
*B01J 19/12*        (2006.01)
*B01J 37/08*        (2006.01)
(Continued)

(52) U.S. Cl.
CPC .......... *B01J 19/126* (2013.01); *B01J 37/344* (2013.01); *C07C 2/76* (2013.01); *C07C 7/12* (2013.01);
(Continued)

(58) Field of Classification Search
CPC ...... B01J 19/126; B01J 37/344; B01J 37/084; B01J 2219/00038; B01J 2208/00442;
(Continued)

(56) References Cited

U.S. PATENT DOCUMENTS 4,279,722 A *  7/1981  Kirkbride .................. B01J 8/42
                                                        204/158.21
5,411,712 A *  5/1995  Woodmansee ......... B01J 19/126
                                                        422/186

(Continued)

FOREIGN PATENT DOCUMENTS

WO    WO-2012121366 A1 *  9/2012    ............. B01J 29/48

*Primary Examiner* — Nicholas A Smith
(74) *Attorney, Agent, or Firm* — Aaron R. Keith; Timothy L. Harney; Michael J. Dobbs

(57) ABSTRACT

Embodiments relate to methods for enhancing chemical conversions. One or more embodiments relate to a method for enhancing a multi-step chemical conversion reaction. The method includes providing a reactant mixture comprising one or more reacting specie(s); and providing a catalyst or sorbent comprising one or more support materials and one or more deposited catalytically active materials. The method further includes applying an electromagnetic field with a prescribed power, frequency, and pulsing strategy specific to interactions of reactant species and an electromagnetic field with at least one of the support materials, sorbent, and catalytically active materials in a particular chemical reaction.

47 Claims, 4 Drawing Sheets

(51) Int. Cl.
*B01J 37/34* (2006.01)
*C07C 2/76* (2006.01)
*C07C 7/12* (2006.01)
*C07C 15/04* (2006.01)
*C07C 15/06* (2006.01)
*C07C 15/08* (2006.01)

(52) U.S. Cl.
CPC .... *B01J 37/084* (2013.01); *B01J 2219/00038* (2013.01); *C07C 15/04* (2013.01); *C07C 15/06* (2013.01); *C07C 15/08* (2013.01)

(58) Field of Classification Search
CPC . B01J 8/0285; B01J 8/025; B01J 23/06; B01J 23/28; B01J 23/92; B01J 27/22; B01J 29/405; B01J 29/48; B01J 29/90; B01J 37/346; B01J 19/129; B01J 2219/00141; B01J 19/00148; C07C 2/76

USPC .................................................. 204/158.14
See application file for complete search history.

(56) References Cited

U.S. PATENT DOCUMENTS

| | | | |
|---|---|---|---|
| 2003/0094452 A1* | 5/2003 | Burkitbaev | B01J 19/12 |
| | | | 219/678 |
| 2008/0210596 A1* | 9/2008 | Litt | B01J 19/0093 |
| | | | 208/20 |
| 2014/0051775 A1* | 2/2014 | Kyle | B01J 19/126 |
| | | | 518/702 |
| 2014/0066676 A1* | 3/2014 | Cheung | B01J 19/24 |
| | | | 422/187 |
| 2015/0004069 A1* | 1/2015 | Ishizuka | H05B 6/806 |
| | | | 422/186 |
| 2017/0120215 A1* | 5/2017 | King | H05B 6/707 |
| 2020/0223692 A1* | 7/2020 | Hamzehlouia | B01J 35/0033 |

* cited by examiner

ELECTROMAGNETIC FIELD-ASSISTED METHOD FOR CHEMICAL CONVERSION

CROSS-REFERENCE TO RELATED APPLICATIONS

This application claims the benefit of and priority to U.S. Provisional Application 62/643,285 filed Mar. 15, 2018, which is incorporated herein by reference in its entirety.

STATEMENT OF GOVERNMENT SUPPORT

The United States Government has rights in this invention pursuant to the employer-employee relationship of the Government to the inventors as U.S. Department of Energy employees and site-support contractors at the National Energy Technology Laboratory.

FIELD OF THE INVENTION

One or more embodiments consistent with the present disclosure relate to chemical or physical conversion. More specifically, embodiments relate to a method of chemical or physical conversion using electromagnetic field (radio frequency/microwave)-assisted processes.

BACKGROUND

The disclosure provides a system and method for chemical conversion using electromagnetic field-assisted catalytic processes.

The ability to selectively produce desired products in a chemical reaction may be greatly improved using catalysts with the application of an electromagnetic field. The general classes of catalytic reactions that may benefit from electromagnetic field-assisted catalysis include overall-endothermic reactions and/or those that contain one or more critical endothermic steps in the reaction mechanism. One example of this class of reaction includes the conversion of natural gas into valuable fuels and chemicals. Natural gas, a cheap and abundant domestic resource, can be upgraded to a wide range of products, including liquid transportation fuels and a wide range of chemical intermediates. To selectively produce these products require using a catalyst with specific surface properties. To produce these products economically non-thermal energy inputs, such as electromagnetic fields, offer significant advantages.

However, methane, the main component of natural gas, is mostly a stable paraffinic compound and it is therefore very challenging to activate the methane molecule particularly in the absence of any oxidant in the feed stream at lower temperatures. The majority of indirect methods used to produce chemicals from methane go through the production of synthesis gas. Whereas, direct methods used to convert methane to valuable chemicals and fuels circumvent the intermediate synthesis gas production step. Therefore, direct methods should have a significant advantage over indirect methods, but, direct methods for methane conversion has not been commercialized yet. There are several technology barriers to be overcome before the direct methane conversion methods can become commercially viable. Those barriers are low methane conversion and product yields, long-term catalyst stability and activity, regeneration of deactivated catalysts, etc.

The thermodynamic limitation of methane conversion reactions may be overcome by using alternative approaches such as electromagnetic field-assisted catalytic reactions. Similarly, other reactions such as Fisher-Tropsch reaction, methane coupling reaction, ammonia synthesis, hydrocarbon reforming, and other similar reactions could be significantly improved in terms of selectivity and conversion by applying microwave fields. Electromagnetic field-assisted reactions also offer unique advantages for converting coal and biomass to value-added chemicals.

Sorbent regeneration rates may also be significantly enhanced by applying electromagnetic (EM) fields (RF/MW) to the sorbent regeneration zone. The EM fields may selectively stimulate targeted sites on the sorbent through dielectric and magnetic interactions without increasing the bulk gas temperature and solid or liquid medium. These conditions may result in significantly higher sorbent regeneration rates at relatively low temperatures than predicted by thermodynamics, which can provide savings in both energy and feed costs. Further, due to the selective input of energy, EM heating may be more efficient and more rapid than conventional heating, which requires heating of the entire reactor system and is limited by conventional heat transfer mechanisms. The basis of these effects lies in the fundamental physics by which EM radiation at radiofrequency/microwave frequencies interacts with matter.

Electromagnetic field-assisted sorbent regeneration could be used for desorbing $CO_2$, $SO_2$, $H_2S$, ammonia, or other adsorbates from solid or liquid sorbents. For carbon capture technology, regeneration using either steam or $CO_2$ may result in slow regeneration kinetics. Regeneration kinetics could be increased with higher regeneration temperatures, which are generally not possible with amine-based sorbents. Heating through electromagnetic radiation is very rapid, likely reaching regeneration temperatures at extremely fast rates. Regeneration would likely be limited to the diffusion of the $CO_2$ away from the sorbent. Because of the rapid regeneration, the physical size of the regenerator would be significantly smaller than the absorber/adsorber in a commercial application, which would be very advantageous for footprint limited power plants and potentially reduce capital costs.

These and other objects, aspects, and advantages of the present disclosure will become better understood with reference to the accompanying description and claims.

SUMMARY

Embodiments of the invention relate to materials, systems, methods of making, and methods of performing chemical conversions. One or more embodiments relate to a method for enhancing a multi-step chemical conversion reaction. The method includes providing a reactant mixture comprising one or more reacting specie(s); and providing a catalyst or sorbent comprising one or more support materials and one or more deposited catalytically active materials. The method further includes applying an electromagnetic field with a prescribed power, frequency, and pulsing strategy specific to interactions of reactant species and an electromagnetic field with at least one of the support materials, sorbent, and catalytically active materials in a particular chemical reaction.

Still other embodiments relate to a method for enhancing a multi-step chemical conversion by applying an electromagnetic field. The method includes performing a chemical reaction with at least one mechanistic step that is endothermic and providing a reactant mixture comprising one or more reacting specie(s). The method further includes providing a catalyst or sorbent comprising one or more support materials and one or more deposited active materials; and applying the electromagnetic field at variable microwave frequencies specific to the interactions of reactant species as well as an electromagnetic field with at least one of the support materials, sorbent and catalytically active materials in a particular chemical reaction.

Other embodiments relate to a method for enhancing a multi-step chemical conversion reaction by applying an electromagnetic field. The method includes performing a chemical reaction with at least one mechanistic step that is endothermic and providing a reactant mixture comprising one or more reacting specie(s). This embodiment further includes providing a catalyst or sorbent comprising one or more support materials and one or more deposited active materials; and applying the electromagnetic field in a pulsed-power mode specific to the interactions of reactant species and electromagnetic field with at least one of the support, sorbent, and catalytically active materials in a particular chemical reaction.

Yet still another embodiment relates to a method for enhancing sorbent regeneration by applying an electromagnetic field. The embodiment includes providing a gas mixture comprising one or more adsorbate specie(s) and providing a sorbent comprising one or more materials and one or more deposited sorption-enhancing active materials. Embodiments further include applying the electromagnetic field having a prescribed power, frequency, and pulsing strategy specific to the interactions of reactant species and electromagnetic field with at least one of the materials, support, sorbent, and/or catalytically active materials in a particular regeneration process.

One or more embodiments include the adsorbate being either chemically or physically absorbed/adsorbed on the sorbent. The sorbent may be either solid or liquid.

The following U.S. Patent Applications are incorporated herein by reference in their entirety:
1. U.S. Pat. No. 8,092,778 to Zhu et al. which discloses a method for producing a hydrogen enriched fuel and carbon nanotubes using microwave assisted methane decomposition on catalyst;
2. U.S. Pat. No. 8,076,869 to Zhu et al. which disclose a method and system for producing a hydrogen enriched fuel using microwave assisted methane decomposition on catalyst;
3. U.S. Pat. No. 8,021448 to Zhu et al. which disclose a method and system for producing a hydrogen enriched fuel using microwave assisted methane plasma decomposition on catalyst;
4. U.S. Pat. No. 5,972,175 to Tanner et al. which disclose a catalytic microwave conversion of gaseous hydrocarbons;
5. U.S. Pat. No. 5,472,581 to Wan which discloses microwave production of C2 hydrocarbons, using a carbon catalyst;
6. U.S. Pat. No.5,256,175 to Murphy which disclose conversion of methane, carbon dioxide and water using microwave radiation
7. U.S. Pat. No. 5,215,634 to Wan et al. which disclose microwave induced catalytic conversion of methane and a hydrating agent to C3 oxygenates
8. U.S. Pat. No.5,205,915 to Ravella et al. which relates to conversion of methane using continuous microwave radiation;
9. U.S. Pat. No. 4,574,038 to Wan which discloses conversion of methane to ethylene and hydrogen using pulsed microwave radiation.

BRIEF DESCRIPTION OF THE DRAWINGS

These and other features, aspects, and advantages of the multiple embodiments of the present invention will become better understood with reference to the following description, appended claims, and accompanied drawings where:

DETAILED DESCRIPTION

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide description of electromagnetic field-enhanced catalysis and methods for using such catalysis.

The underlying objective of using electromagnetic field-enhanced catalysis is twofold. First, the electromagnetic (EM) field provides targeted heating of the active metal sites of the catalyst, thereby enhancing the catalytic activity without increasing the bulk temperature of the surrounding reactants. Therefore, the methane activation reaction may be initiated at the active metal sites or 'hot spots' while the bulk temperature might be significantly lower than the hot spots and, hence, enhancing the methane activity that is limited by thermodynamics. Second, the EM field plays the role of catalyst promoter. The photon energy in electromagnetic radiation at RF and microwave frequencies is not sufficient for any bond cleavage.

Figure 1:
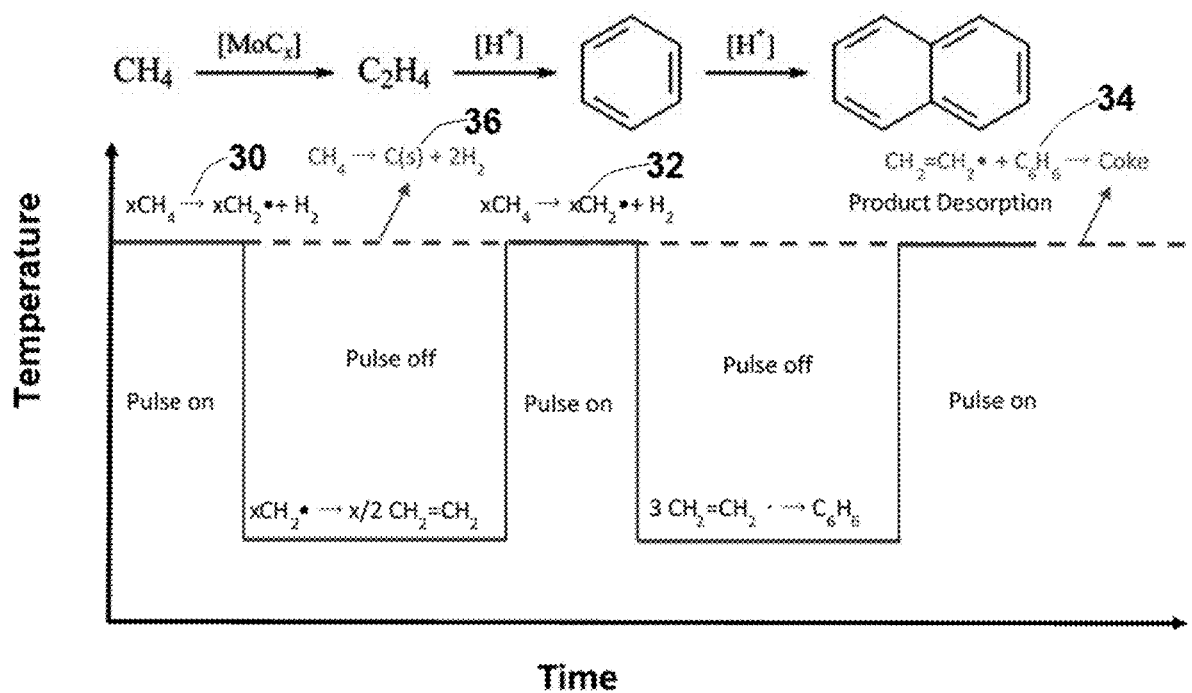
FIG. 1 depicts a schematic illustrating an exemplary reaction of the reaction of methane dehydroaromatization.
Figure 2:
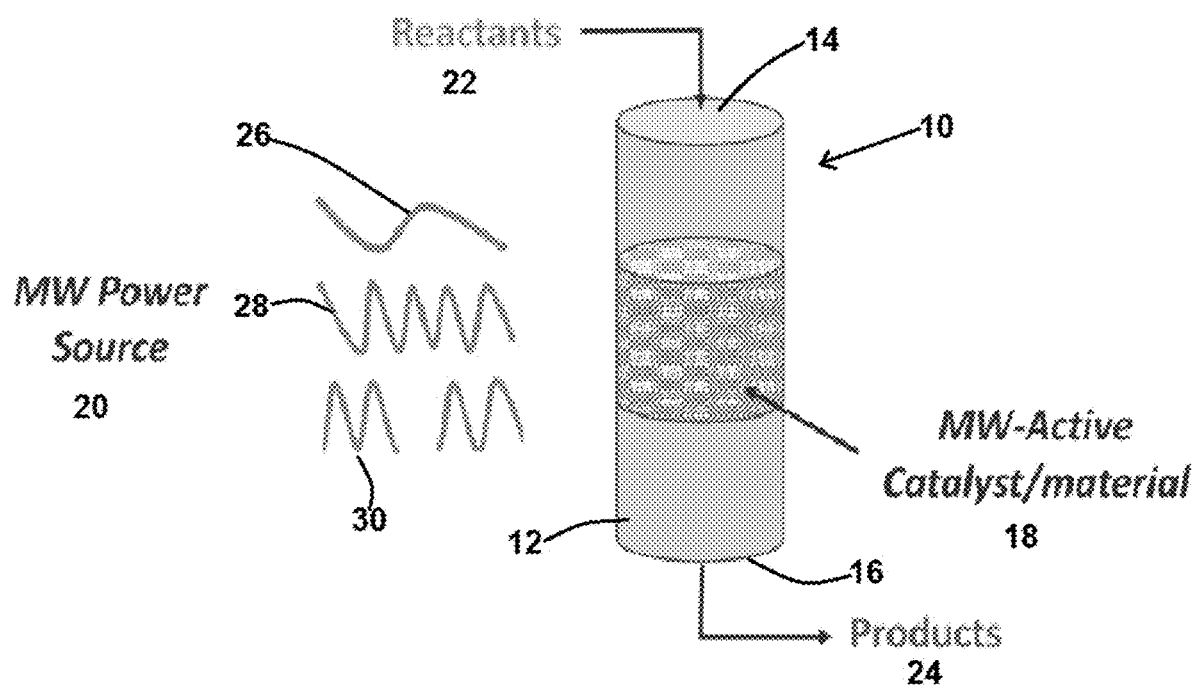
FIG. 2 depicts a schematic of microwave reactor system.

However, the EM field may induce the polarization of reactant molecules within the catalyst material and, hence, result in a weakened bond that may be cleaved relatively easier. Additionally, the EM field can induce electric and/or magnetic fields in between absorptive sites within the catalyst/adsorbent/absorbent/MW active material contributing to lower activation energies, electron donation, and relaxing bonds. The catalyst selectivity may be further tuned by using an appropriate electromagnetic energy pulsing scheme. Electromagnetic energy is operated in a "pulsed-power" mode; higher-power pulse time activates the reactive species on the catalyst sites to start the reaction; low-power pulse time maintains a lower reaction temperature to promote the desired reaction mechanism as illustrated in FIG. 1. For example, in dehydroaromatization reaction as shown in FIG. 2, the C—H bond cleavage in methane ($xCH_4 \Rightarrow xCH_2^* + H_2$, designated 30 in FIG. 1), an endothermic step, occurs at a 'hot spot' created by the electromagnetic fields. During the pulse-off situation, the 'hot spot' gives up its heat, attaining a lower energy state which is favorable for C—C bond formation ($xCH_2 \Rightarrow x/2\ CH_2 = CH_2$ and $CH_2 = CH_2 \Rightarrow C_6H_6$; designated 32 and 34 respectively in FIG. 1), an exothermic step, but unfavorable for further C—H cleavage ($CH_4 \Rightarrow C(s) + 2H_2$, designed 36 in FIG. 1), an endothermic step, in methyl radicals. Due to selective heating, the electromagnetic heating is more energy efficient and faster compared to the conventional heating in which the reactor is heated first and then the heat is transferred to the reaction medium by convection. Electromagnetic power and/or frequency may be tuned to selectively activate specific reaction sites and reaction species. The frequency dependency is illustrated in Table 1 below:

TABLE 1

Frequency interactions with catalyst and reactants

| Case # | Reactants | Catalyst | Frequency | Description |
|---|---|---|---|---|
| 1 | $R_{1,0} + R_{2,0}$ | A A<br>A A | $F_{1A}$ | There is a flow of two reactant species, $R_{1,0}$ and $R_{2,0}$, interacting with a single catalytic site A. The EM is operating at one frequency, $F_1$ and is coupled with the catalytic sites, A, to enhance the conversion of the reactants on the catalyst surface. |
| 2 | $R_{1,0} + R_{2,0}$ | A B<br>B A | $F_{1A} + F_{2B}$ | There is a flow of two reactant species, $R_{1,0}$ and $R_{2,0}$, which interact with catalytic sites A and B, respectively. The EM operates at two different frequencies ($F_1$ and $F_2$), simultaneously or alternating, where $F_1$ couples with catalytic site A and $F_2$ couples with catalytic site B, to enhance the conversion of the reactants on the catalyst surface. |
| 3 | $R_{1,p} + R_{2,0}$ | A A<br>A A | $F_{1p} + F_{2A}$ | There is a flow of two reactant species, $R_{1,p}$ and $R_{2,0}$, which interact with a single catalytic site A. The EM operates at two different frequencies ($F_1$ and $F_2$), where $F_1$ couples with reactant species p and $F_2$ couples with catalytic site A, to enhance conversion of the reactants on the catalyst surface. |
| 4 | $R_{1,p} + R_{2,q}$ | A A<br>A A | $F_{1p} + F_{2q} + F_{3A}$ | There is a flow of two reactant species, $R_{1,p}$ and $R_{2,q}$, which interact with a single catalytic site A. The EM operates at three different frequencies ($F_1$, $F_2$, and $F_3$), where $F_1$ couples with reactant species p, $F_2$ couples with reactant species q, and $F_3$ couples with catalytic site A, to enhance conversion of the reactants on the catalyst surface. |

FIG. 2 depicts an apparatus 10 using microwaves (MW) as a heating source compare to a conventional thermal heating source on which the methane conversion into aromatic compounds (mainly benzene) was evaluated. The apparatus 10 includes a fixed-bed continuous-flow reactor 12. The reactor 12 has openings 14 and 16 receiving reactants 22 and outputting products 24 respectively, and includes a catalyst bed 18. A microwave system or power source 20 is illustrated and used as a heating source. In at least one embodiment, it is contemplated that the microwave system 20 provides different types of pulse modes including, for example, low-frequency continuous_mode designated 26, high-frequency continuous mode designated 26 and pulsed-on and pulsed-off mode designated 30.

In at least one embodiment, methane gas was used as the reactant gas 22 supplied to opening 14. Different forms of Mo (Mo oxide, Mo carbide, and the like) supported on HZSM-5 powders were used in the reactor 12. Two different concentrations 4% Mo and 6% Mo supported on HZSM5 were used. A 3 wt % Zn supported catalyst was also used. In one or more embodiments, the active catalyst materials were mixed with a microwave active material, silicon carbide (50 wt % catalyst+50% silicon carbide). Silicon carbide does not have any catalytic activity for the desired reaction. Catalysts were prepared by pressing and sieving the mixture powder between 300 to 600 microns to prevent plugging the reactor. Experiments were conducted at a WHSV of 2500 scc/gcat/hr, microwave power input between 200-350 W with 500 ms pulsing (50% pulsing rate), and atmospheric pressure. Where, the pulsing rate (duty cycle) is given as the ratio of the pulse ON time to the total pulse time period.

$$\text{pulsing rate} = \frac{t_{on}}{t_{on} + t_{off}} * 100$$

Where $t_{on}$ is the time during the microwave power is on and $t_{off}$ is the time during the microwave is off.

The product stream 24 from the microwave reactor 12 (unconverted methane, $N_2$, ethane, ethylene, benzene, and hydrogen) was analyzed using a microGC. Yield of benzene was defined as:

Yield of benzene (%)=moles of benzene produced× 6×100/moles of methane fed

Table 2 depicts the comparison of benzene formation over different catalysts with and without microwave heating. There is a fundamental difference in benzene formation from methane in the presence of microwave. The difference was significant particularly for Zn-based catalyst; a maximum yield of 0.9% was obtained from conventional heating for all condition studied in our labs (space velocity 750 to 6000 $hr^{-1}$ and temperature 650-750° C.). The microwave heating is particularly viable for the catalysts which are susceptible t metal loss due to high volatility at the reaction temperature. The Mo/H-ZSM5 zeolite is a widely reported catalyst for the single-step methane aromatization process. It is believed that molybdenum carbide is an active phase for the dehydroaromatization (DHA) reaction. Coke formation is inevitable during the DHA reaction. Therefore, regeneration of the deactivated catalyst has to be performed for frequent coke burn offs. The active phase, molybdenum carbide, converts into molybdenum oxide during regeneration. Therefore, the catalyst has to be reactivated to the carbide form after each regeneration cycle. Although, activity of Zn-based catalyst is significantly lower than Mo-based catalyst; but the active phase, zinc oxide, does not change during regeneration and, hence, it does not require activation after each regeneration cycle. But, the Zn-catalyst suffers metal loss at the reaction temperature due to its higher volatility. However, in a microwave system, the desired reaction may be conducted at relatively low bulk temperatures where the metal loss is not significant. Thus, electromagnetic field-assisted catalysis process provides a significant advantage over the traditional heating process for such systems.

TABLE 2

Results of methane dehydroaromatization reaction with and without microwave

| Run # | Catalyst bed | Benzene yield (%) MW | Benzene yield (%) Non-MW* | MW power, pulse time |
|---|---|---|---|---|
| A | (5 g of 4 wt % Mo/ HZSM5 + $Mo_2C$) + 5 g SiC (Oxide:carbide = 1:1) | 1.3 | | 150 W, 500 ms |
| B | 5 g of 4 wt % $MoO_3$/ HZSM5 + 5 g SiC | 6.4 | 4.2 | 200 W, 500 ms |
| C | 5 g of 4 wt % $Mo_2C$/ HZSM5 | 0.4 | | 200 W, 500 ms |
| D | 5 g of 3 wt % Zn/ HZSM5 + 5 g SiC | 1.7 | 0.9 | 200 W, 500 ms |
| E | 5 g of 6 wt % Mo/ HZSM5 + 5 g SiC | 5.0 | 3.8 | 200 W, 500 ms |

Electromagnetic energy provides targeted heating of the active metal sites of a catalyst, thereby enhancing the catalytic activity without increasing the bulk temperature of the surrounding reactants. Therefore, the methane activation reaction may be initiated at the active metal sites or 'hot spots' while the bulk temperature might be significantly lower than the hot spots and, hence, enhancing the methane activity that was limited by thermodynamics.

EM fields act as the catalyst promoter. The energy in EM radiation at RF and microwave frequencies is not sufficient for any bond cleavage. However, the EM field may induce the polarization of reactant molecules within the catalyst material and result in a weakened bond that can be cleaved relatively easier. Additionally, the EM field can induce electric and/or magnetic fields inbetween absorptive sites within the catalyst/abosorbant/MW active material contributing to lower activation energies, electron donation, and relaxing bonds. The catalyst selectivity can be further tuned by using an appropriate EM field pulsing scheme. The C—H bond cleavage in methane, an endothermic process, occurs at a 'hot spot' created by the EM field. During the pulse off situation, the 'hot spot' gives away its heat and attains a lower energy state which is favorable for C—C bond formation, an exothermic process, but unfavorable for further C—H cleavage in methyl radicals. Due to selective heating, the EM heating is more energy efficient and faster compared to the conventional heating in which the reactor is heated first and then the heat is transferred to the reaction medium by convection, conduction and IR radiation.

Electromagnetic energy can directly heat mixtures of catalyst and microwave active materials by coupling an oscillating electromagnetic field with the material's internal structure. The stimulation of catalytic reactions using electromagnetic energy has been shown to alter the selectivity of reactions because the local gas temperatures remain lower than the solids temperatures and secondary gas phase reactions can be suppressed. This process has advantages over traditional radiant heating because heat is more efficiently injected directly to the catalyst and less overall energy is required to heat the reaction zone to the desired temperatures. Therefore, the EM process can be used to enhance the selectivity and yield of natural gas conversion processes.

Several parameters such as active catalytic sites and support, electromagnetic power and pulsing scheme, and the physical properties of the catalyst material (dielectric properties, etc.) that may affect the methane conversion and product formation were evaluated. The focus within this project was on EM field-enhanced catalytic methane conversion into olefins and aromatics, but extrapolation beyond this application into many chemical processes is expected. Particularly, selectivity of desired products from a reaction could be significantly affected by applied electromagnetic field with different frequency as well as pulsing scheme.

In addition to the natural gas dehydroaromatization reaction, the Fisher-Tropsch reaction, methane coupling reaction, ammonia synthesis, hydrocarbon reforming, and other similar reactions could be significantly improved in terms of selectivity and conversion by applying electromagnetic fields.

Some other reactions but not limited to can be carried out using the electromagnetic method described in this disclosure are listed in Table 3.

TABLE 3

Other Possible Reactions

| Reaction | Equation | Endo/Exothermic |
|---|---|---|
| Non-oxidative methane dehydroaromatization | $6 CH_4 \leftrightarrow C_6H_6 + 9 H_2$ | Endo (Delta H = 596 kJ/mol) |
| Non-oxidative coupling of methane | $2 CH_4 \leftrightarrow C_2H_4 + 2H_2$ | Endo (Delta H = 202 kJ/mol) |
| Oxidative coupling of methane | $2CH_4 + O_2 \leftrightarrow C_2H_4 + 2H_2O$ | Exo (Delta H = −455 kJ/mol) |
| Fischer-Tropsch | $nCO + 2n H_2 \leftrightarrow C_nH_{2n} + n H_2O$ | Exo (Delta H = −165 kJ/mol) |
| Methane dry reforming | $CH_4 + CO_2 \leftrightarrow 2 CO + 2 H_2$ | Endo (Delta H = 247 kJ/mol) |
| Methane steam reforming | $CH_4 + H_2O \leftrightarrow CO + 3 H_2$ | Endo (Delta H = 226 kJ/mol) |
| Hydrocarbon decomposition reaction | $C_nH_m \rightarrow nC + m/2 H_2$ | Endo (Delta H > 0) |
| Ammonia synthesis | $N_2 + 3H_2 \leftrightarrow 2NH_3$ | Exo (Delta H = −46 kJ/mol) |
| NOx decomposition reaction | $NOx \leftrightarrow N_2 + x/2 O_2$ | Exo (Delta H < 0) |

Figure 3:
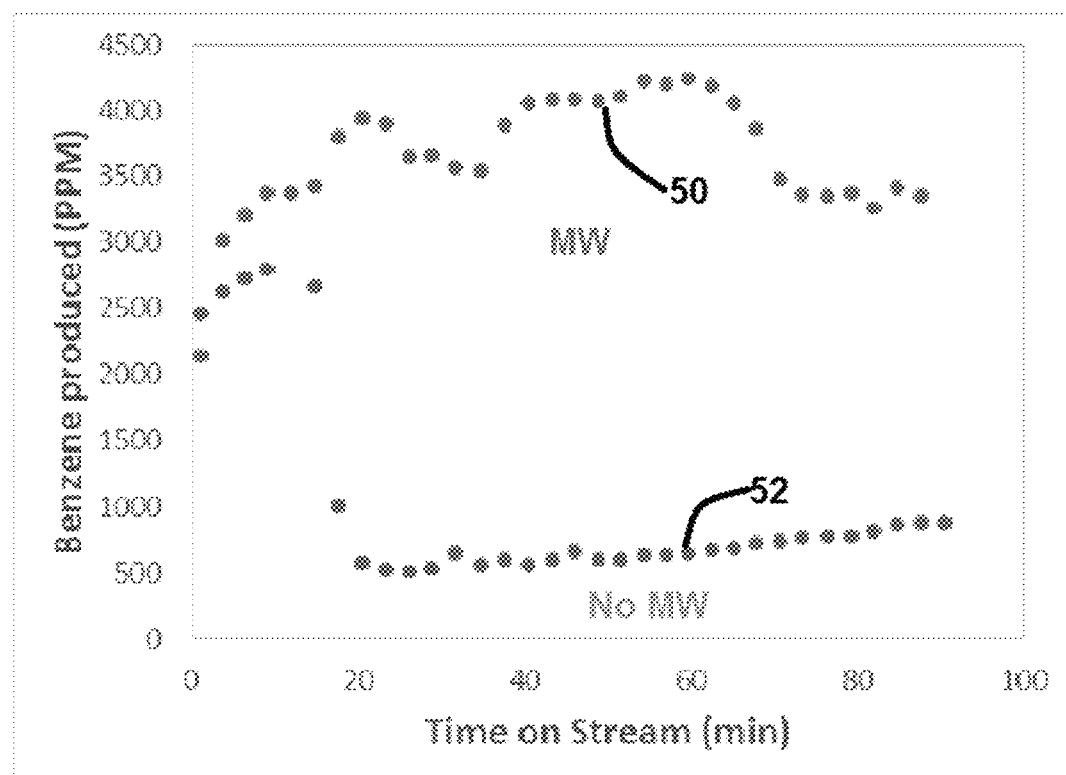
FIG. 3 depicts a graph illustrating benzene production using coal and methane with and without microwaves.

FIG. 3 depicts a graph illustrating benzene production using coal and methane. FIG. 3 illustrates such benzene production with microwaves (line 50) and without microwaves (line 52). FIG. 3 indicates that benzene production with microwaves is improved in comparison to benzene production without microwaves.

Figure 4:
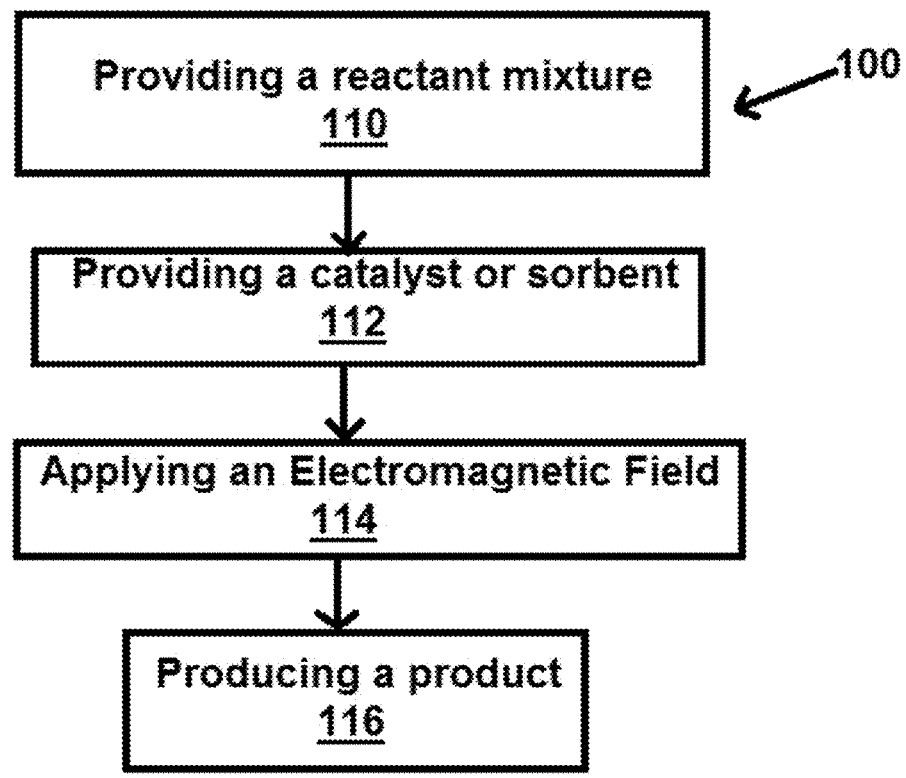
FIG. 4 depicts a high level flow diagram of one method of enhancing a chemical conversion.

FIG. 4 depicts a high level flow diagram of one method, generally designated 100, for enhancing a chemical conversion. The method 100 for enhancing the chemical conversion includes providing a reactant mixture, step 110 and providing a catalyst or sorbent, step 112. Method 100 further includes applying an electromagnetic field, step 114. Finally, the method 100 includes producing one or more products, step 116.

One or more embodiments relate to a method 100 for enhancing a multi-step chemical conversion reaction. The method 100 includes providing a reactant mixture comprising one or more reacting specie(s); and providing a catalyst or sorbent comprising one or more support materials and one or more deposited catalytically active materials. The method 100 further includes applying an electromagnetic field with a prescribed power, frequency, and pulsing strategy specific to interactions of reactant species and an electromagnetic field with at least one of the support materials, sorbent, and catalytically active materials in a particular chemical reaction.

Still other embodiments relate to a method 100 for enhancing a multi-step chemical conversion by applying an electromagnetic field. The method 100 includes performing a chemical reaction with at least one mechanistic step that is endothermic and providing a reactant mixture comprising one or more reacting specie(s). The method 100 further includes providing a catalyst or sorbent comprising one or more support materials and one or more deposited active materials; and applying the electromagnetic field at variable microwave frequencies specific to the interactions of reactant species as well as an electromagnetic field with at least one of the support materials, sorbent and catalytically active materials in a particular chemical reaction.

Other embodiments relate to a method 100 for enhancing a multi-step chemical conversion reaction by applying an electromagnetic field. The method 100 includes performing a chemical reaction with at least one mechanistic step that is endothermic and providing a reactant mixture comprising one or more reacting specie(s). This embodiment further includes providing a catalyst or sorbent comprising one or more support materials and one or more deposited active materials; and applying the electromagnetic field in a pulsed-power mode specific to the interactions of reactant species and electromagnetic field with at least one of the support, sorbent, and catalytically active materials in a particular chemical reaction.

Yet still another embodiment relates to a method 100 for enhancing sorbent regeneration by applying an electromagnetic field. The embodiment includes providing a gas mixture comprising one or more adsorbate specie(s) and providing a sorbent comprising one or more materials and one or more deposited sorption-enhancing active materials. Embodiments further include applying the electromagnetic field having a prescribed power, frequency, and pulsing strategy specific to the interactions of reactant species and electromagnetic field with at least one of the materials, support, sorbent, and/or catalytically active materials in a particular regeneration process.

One or more exemplary embodiments includes an endothermic or exothermic chemical reaction, where the chemical reaction includes a plurality of reaction mechanism steps performed in parallel or series leading to undesired side products. The electromagnetic field may be removed or reduced to minimize the undesired, parallel or series side reaction mechanisms and product formation.

In at least one embodiment, the electromagnetic field occurs over a frequency ranging from about 3 KHz to about 300 GHz. Alternatively, the electromagnetic field occurs by sweeping the frequency over the 3 KHz to 300 GHz range, where the reaction occurs at two or more frequencies ranging from about 3 KHz to 300 GHz, where the reaction occurs at two or multiple frequencies simultaneously or alternatively ranging from about 3 KHz to 300 GHz.

Embodiments may include the electromagnetic field being applied to the reaction at a pulsing time ranging from about 1 to 99% or more specifically from about 1 to 75%. In one or more embodiments, the electromagnetic field may be applied to the chemical reaction at a pulsing rate related to the thermodynamics of the chemical reaction such that the pulsing rate is lower for a reaction step that is highly exothermic and the pulsing rate is higher for a reaction step that is less exothermic.

In one or more embodiments of method 100, the chemical reaction includes hydrocarbon conversion to benzene, toluene, and xylenes, where the hydrocarbon conversion is $C_nH_m$ where n=1 to 20 and m≥n+2 for example (although one embodiment contemplates m≤n+2). Embodiments include the chemical reaction encompassing ammonia synthesized from nitrogen and hydrogen; hydrogenation of CO into hydrocarbons; hydrocarbon conversion in the presence of an oxidant to syngas; hydrocarbon conversion in the presence of an oxidant to syngas, where the oxidant may be selected from a group comprising at least steam, $CO_2$, and air; oxidative coupling of methane; methane decomposition into solid carbon and hydrogen; NOx decomposition; desulfurization; coal pyrolysis and/or gasification to syngas, liquid fuels and chemicals, and other valuable carbon products.

One or more embodiments of method 100 includes a char used both as a reactant and catalytic material. Embodiments of the char source is coal and/or biomass.

Embodiments of method 100 include an adsorbate being chemically or physically absorbed/adsorbed on the sorbent. The sorbent may be solid or liquid.

Having described the basic concept of the embodiments, it will be apparent to those skilled in the art that the foregoing detailed disclosure is intended to be presented by way of example. Accordingly, these terms should be interpreted as indicating that insubstantial or inconsequential modifications or alterations and various improvements of the subject matter described and claimed are considered to be within the scope of the spirited embodiments as recited in the appended claims. Additionally, the recited order of the elements or sequences, or the use of numbers, letters or other designations therefor, is not intended to limit the claimed processes to any order except as may be specified. All ranges disclosed herein also encompass any and all possible sub-ranges and combinations of sub-ranges thereof. Any listed range is easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as up to, at least, greater than, less than, and the like refer to ranges which are subsequently broken down into sub-ranges as discussed above. As utilized herein, the terms "about," "substantially," and other similar terms are intended to have a broad meaning in conjunction with the common and accepted usage by those having ordinary skill in the art to which the subject matter of this disclosure pertains. As utilized herein, the term "approximately equal to" shall carry the meaning of being within 15, 10, 5, 4, 3, 2, or 1 percent of the subject measurement, item, unit, or concentration, with preference given to the percent variance. It should be understood by those of skill in the art who review this disclosure that these terms are intended to allow a description of certain features described and claimed without restricting the scope of these features to the exact numerical ranges provided. Accordingly, the embodiments are limited only by the following claims and equivalents thereto. All publications and patent documents cited in this application are incorporated by reference in their entirety for all purposes to the same extent as if each individual publication or patent document were so individually denoted.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

We claim:

1. A method for enhancing a multi-step chemical conversion reaction comprising: providing a gaseous reactant mixture comprising one or more reacting specie(s); providing a catalyst or sorbent comprising one or more support materials and one or more deposited catalytically active materials, wherein the catalyst comprises catalytic sites; and applying an electromagnetic field with a prescribed power, frequency, and pulsing strategy specific to interactions of reactant species and an electromagnetic field with at least one of the support materials, sorbent, and catalytically active materials in a particular chemical reaction, wherein the applied electromagnetic field simultaneously comprises a first frequency and a second frequency, wherein the first frequency selectively activates the one or more catalytically active materials, wherein the second frequency selectively activates the one or more support materials, wherein the applying an electromagnetic field step comprises selectively heating said catalytic sites, and wherein the selective heating of said catalytic sites does not increase the bulk temperature of reacting specie(s) surrounding said catalytic sites.

2. The method of claim 1 wherein the chemical reaction is an endothermic chemical reaction.

3. The method of claim 2 wherein the endothermic chemical reaction includes a plurality of reaction mechanism steps performed in parallel leading to desired products.

4. The method of claim 3 wherein the electromagnetic field is removed or reduced to minimize the undesired side reactions and maximize desired product formations.

5. The method of claim 2 wherein the endothermic chemical reaction includes a plurality of reaction mechanism steps performed in series leading to desired products.

6. The method of claim 5 wherein the electromagnetic field is removed or reduced to minimize the subsequent undesired reaction mechanism steps and maximize desired product formation.

7. The method of claim 2 wherein the support material does not appreciably absorb the electromagnetic field.

8. The method of claim 2 wherein the support material appreciably absorbs the electromagnetic field.

9. The method of claim 2 wherein the deposited catalytically active material does not appreciably absorb the electromagnetic field.

10. The method of claim 2 wherein the deposited catalytically active material absorbs the electromagnetic field.

11. The method of claim 2 wherein the sorbent material does not appreciably absorb electromagnetic field.

12. The method of claim 2 wherein the sorbent material does appreciably absorb the electromagnetic field.

13. The method of claim 1 wherein the chemical reaction is an exothermic chemical reaction.

14. The method of claim 13 wherein the exothermic chemical reaction includes a plurality of reaction mechanism steps performed in series leading to desired side products.

15. The method of claim 14 wherein the application of the electromagnetic field is removed or reduced to minimize the desired side reactions and maximize the desired product formations.

16. The method of claim 13 wherein the electromagnetic field is removed or reduced to minimize the subsequent reaction mechanism steps and product formation.

17. The method of claim 1 wherein the electromagnetic field is applied over a frequency ranging from about 3 KHz to about 300 GHz.

18. The method of claim 1 wherein the electromagnetic field is applied by sweeping a frequency ranging from about 3 KHz to 300 GHz.

19. The method of claim 1 wherein the electromagnetic field is applied to the chemical reaction by performing the reaction at two or more frequencies ranging from about 3 KHz to 300 GHz.

20. The method of claim 19 wherein the electromagnetic field is applied to the chemical reaction by performing the reaction at two or multiple frequencies simultaneously ranging from about 3 KHz to 300 GHz.

21. The method of claim 19 wherein the electromagnetic field is applied to the chemical reaction by performing the reaction at two or multiple frequencies alternatively ranging from about 3 KHz to 300 GHz.

22. The method of claim 1 wherein the electromagnetic field is applied to the chemical reaction at a pulsing rate related to the thermodynamics of the chemical reaction such that the pulsing rate is lower for a reaction step that is highly exothermic and the pulsing rate is higher for a reaction step that is less exothermic.

23. The method of claim 1 wherein the chemical reaction comprises hydrocarbon conversion to benzene, toluene, and xylenes.

24. The method of claim 1 wherein the hydrocarbon conversion is $sC_nH_m$ where n=1 to 20 and m≥2n+2.

25. The method of claim 1 where the chemical reaction comprises ammonia synthesized from nitrogen and hydrogen.

26. The method of claim 1 where the chemical reaction comprises at least one or hydrogenation of CO into hydrocarbons and oxygenated hydrocarbons.

27. The method of claim 1 where the chemical reaction comprises hydrocarbon conversion in the presence of an oxidant to syngas.

28. The method of claim 27 wherein the oxidant is selected from a group comprising at least steam, $CO_2$, and air.

29. The method of claim 1 wherein the chemical reaction comprises oxidative coupling of methane.

30. The method of claim 1 wherein the chemical reaction comprises methane decomposition into solid carbon and hydrogen.

31. The method of claim 1 wherein the chemical reaction comprises NOx decomposition.

32. The method of claim 1 wherein the chemical reaction comprises desulfurization.

33. The method of claim 1 wherein the chemical reaction comprises coal pyrolysis and/or gasification to syngas, liquid fuels and chemicals, and other valuable carbon products.

34. The method of claim 1 further includes a char used both as a reactant and catalyst.

35. The method of claim 34 wherein the char source is coal.

36. The method of claim 34 wherein the char source is biomass.

37. The method of claim 1 wherein the electromagnetic field is applied to the chemical reaction at a pulsing time ranging from about 1 to 99%.

38. The method of claim 37 wherein the electromagnetic field is applied to the chemical reaction at a pulsing time ranging from about 1 to 75%.

39. The method of claim 1 wherein the applied electromagnetic field further simultaneously comprises a third frequency wherein the third frequency selectively activates a third material selected from the group consisting of: the one or more reacting specie(s), the catalytically active materials, and the support materials, and wherein the first, second, and third materials are all different materials.

40. A method for enhancing a multi-step chemical conversion by applying an electromagnetic field comprising: performing a chemical reaction with at least one mechanistic step that is endothermic; providing a gaseous reactant mixture comprising one or more reacting specie(s); providing a catalyst or sorbent comprising one or more support materials and one or more deposited active materials, wherein the catalyst comprises catalytic sites; and applying the electromagnetic field at simultaneous microwave frequencies specific to the interactions of reactant species as well as an electromagnetic field with at least one of the support materials, sorbent and catalytically active materials in a particular chemical reaction, wherein the simultaneous microwave frequencies comprise a first frequency and a second frequency, wherein the first frequency selectively activates a the one or more catalytically active materials wherein the second frequency selectively activates support materials, wherein the applying the electromagnetic field step comprises selectively heating said catalytic sites, and wherein the selective heating of said catalytic sites does not increase the bulk temperature of reacting specie(s) surrounding said catalytic sites.

41. The method of claim 40 wherein the electromagnetic field is applied to the chemical reaction at a pulsing time ranging from about 1 to 99%.

42. The method of claim 41 wherein the electromagnetic field is applied to the chemical reaction at a pulsing time ranging from about 1 to 75%.

43. The method of claim 40 wherein the simultaneous microwave frequencies further comprise a third frequency, wherein the third frequency selectively activates a third material selected from the group consisting of: the one or more reacting specie(s), the catalytically active materials, and the support materials, and wherein the first, second, and third materials are all different materials.

44. A method for enhancing a multi-step chemical conversion reaction by applying an electromagnetic field comprising: performing a chemical reaction with at least one mechanistic step that is endothermic; providing a gaseous reactant mixture comprising one or more reacting specie(s); providing a catalyst or sorbent comprising one or more support materials and one or more deposited active materials, wherein the catalyst comprises catalytic sites; and applying the electromagnetic field in a pulsed-power mode specific to the interactions of reactant species and electromagnetic field with at least one of the support, sorbent, and catalytically active materials in a particular chemical reaction, wherein the applied electromagnetic field simultaneously comprises a first frequency and a second frequency, wherein the first frequency selectively activates the one or more catalytically active materials wherein the second frequency selectively activates the one or more support materials, wherein the applying an electromagnetic field step comprises selectively heating said catalytic sites, and wherein the selective heating of said catalytic sites does not increase the bulk temperature of reacting specie(s) surrounding said catalytic sites.

45. The method of claim 44 wherein the pulsed-power mode comprises applying the electromagnetic field to the chemical reaction at a pulsing time ranging from about 1 to 99%.

46. The method of claim 45 wherein the pulsed-power mode comprises applying the electromagnetic field to the chemical reaction at a pulsing time ranging from about 1 to 75%.

47. The method of claim 44 wherein the applied electromagnetic field further simultaneously comprises a third frequency, wherein the third frequency selectively activates a third material selected from the group consisting of: the one or more reacting specie(s), the catalytically active materials, and the support materials, and wherein the first, second, and third materials are all different materials.

* * * * *